US006858001B1

(12) United States Patent
Aboul-Hosn

(10) Patent No.: US 6,858,001 B1
(45) Date of Patent: Feb. 22, 2005

(54) SINGLE PORT CARDIAC SUPPORT APPARATUS

(75) Inventor: Walid Najib Aboul-Hosn, Fair Oaks, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 09/669,104

(22) Filed: Sep. 25, 2000

Related U.S. Application Data

(62) Division of application No. 08/891,456, filed on Jul. 11, 1997, now Pat. No. 6,123,725.

(51) Int. Cl.[7] .............................................. A61M 1/10
(52) U.S. Cl. ...................... 600/16; 623/3.13; 623/3.25; 415/900
(58) Field of Search ................... 600/16–18; 604/93.01, 604/96.01, 97.01–97.03, 98.01, 98.02, 99.01–99.03, 101.01, 101.05, 102.02, 102.03, 103.01, 103.07, 43, 509, 510, 151, 536, 266, 27, 28, 284, 914, 915, 919; 623/3.13, 3.14, 3.24, 3.25, 3.26, 3.3, 3.1; 415/900

(56) References Cited

U.S. PATENT DOCUMENTS

| | | |
|---|---|---|
| 2,669,668 A | 2/1954 | Okulitch et al. |
| 3,487,784 A | 1/1970 | Rafferty et al. |
| 3,608,088 A | 9/1971 | Dorman et al. |
| 3,626,947 A | 12/1971 | Sparks |
| 3,647,324 A | 3/1972 | Rafferty et al. |
| 3,771,627 A | 11/1973 | Ruisi |
| 3,864,055 A | 2/1975 | Kletschka et al. |
| 3,896,501 A | 7/1975 | Bifano et al. |
| RE28,742 E | 3/1976 | Rafferty et al. |
| 3,957,389 A | 5/1976 | Rafferty et al. |
| 3,970,408 A | 7/1976 | Rafferty et al. |
| 3,995,617 A | 12/1976 | Watkins et al. |

(List continued on next page.)

FOREIGN PATENT DOCUMENTS

| | | |
|---|---|---|
| CA | 1 222 355 | 6/1987 |
| CA | 1 240 802 | 8/1988 |
| CA | 1 302 829 | 6/1992 |

(List continued on next page.)

OTHER PUBLICATIONS

Takami, Yoshiyuki, et al., "Effect of Surface Roughness on Hemolysis in a Centrifugal Blood Pump", ASAIO Journal; vol. 42 pp. M858–N862.

Takami, Yoshiyuki, et al., "Effect of Surface Roughness on Hemolysis in a Pivot Bearing Supported Gyro Centrifugal Pump (C1E3)", Artificial Organs; vol. 20, No. 11, pp. 1156–1161, 1996.

Takami, Yoshiyuki, et al., "Material of the Double Pivot Bearing System in the Gyro C1E3 Centrifugal Pump", Artificial Organs, vol. 21, No. 2, pp. 143–147, 1997.

(List continued on next page.)

*Primary Examiner*—Angela D. Sykes
*Assistant Examiner*—Joseph S. Machuga
(74) *Attorney, Agent, or Firm*—Ryan Kromholz & Manion, S.C.

(57) ABSTRACT

A minimal intrusive cardiac support apparatus is disclosed which requires only one incision into a main blood vessel or heart chamber. The apparatus includes a pair of generally coaxial and slideably arranged cannulae (one inner and one outer) communicatively coupled to a blood pump for providing right-heart and/or left-heart cardiac support during cardiac surgery. Optional balloons may be mounted on the outside of the inner and outer conduits which can be selectively inflated to seal off the sides surrounding vessel or to deliver cooling fluid or medication to the surrounding tissue. Using the apparatus, a method of pumping blood through the body is also disclosed.

7 Claims, 5 Drawing Sheets

U.S. PATENT DOCUMENTS

| | | |
|---|---|---|
| 4,086,665 A | 5/1978 | Poirier |
| 4,105,016 A | 8/1978 | Donovan, Jr. |
| 4,108,161 A | 8/1978 | Samuels et al. |
| 4,116,589 A | 9/1978 | Rishton |
| 4,118,806 A | 10/1978 | Porier et al. |
| 4,129,129 A | 12/1978 | Amrine |
| 4,135,253 A | 1/1979 | Reich et al. |
| 4,173,796 A | 11/1979 | Jarvik |
| 4,275,988 A | 6/1981 | Kalashnikov et al. |
| 4,382,199 A | 5/1983 | Isaacson |
| 4,403,983 A | 9/1983 | Edelman et al. |
| 4,451,252 A | 5/1984 | Martin |
| 4,507,048 A | 3/1985 | Belenger et al. |
| 4,512,726 A | 4/1985 | Strimling |
| 4,567,882 A | 2/1986 | Heller |
| 4,589,822 A | 5/1986 | Clausen et al. |
| 4,606,698 A | 8/1986 | Clausen et al. |
| 4,625,712 A * | 12/1986 | Wampler .................... 600/16 |
| 4,648,865 A | 3/1987 | Aigner |
| 4,688,998 A | 8/1987 | Olsen et al. |
| 4,693,243 A * | 9/1987 | Buras .................... 128/207.15 |
| 4,704,121 A | 11/1987 | Moise |
| 4,705,501 A | 11/1987 | Wigness et al. |
| 4,753,221 A | 6/1988 | Kensey et al. |
| 4,769,031 A | 9/1988 | McGough et al. |
| 4,779,614 A | 10/1988 | Moise |
| 4,817,586 A | 4/1989 | Wampler |
| 4,844,707 A | 7/1989 | Kletschka |
| 4,846,152 A | 7/1989 | Wampler et al. |
| 4,895,557 A | 1/1990 | Moise et al. |
| 4,898,518 A | 2/1990 | Hubbard et al. |
| 4,906,229 A | 3/1990 | Wampler |
| 4,908,012 A | 3/1990 | Moise et al. |
| 4,919,647 A | 4/1990 | Nash |
| 4,925,377 A | 5/1990 | Inacio et al. |
| 4,927,407 A | 5/1990 | Dorman |
| 4,944,722 A | 7/1990 | Carriker et al. |
| 4,944,748 A | 7/1990 | Bramm et al. |
| 4,946,440 A * | 8/1990 | Hall .................... 604/164.09 |
| 4,950,259 A | 8/1990 | Geary et al. |
| 4,955,856 A | 9/1990 | Phillips |
| 4,955,861 A | 9/1990 | Enegren et al. |
| 4,957,504 A | 9/1990 | Chardack |
| 4,969,865 A | 11/1990 | Hwang et al. |
| 4,984,972 A | 1/1991 | Clausen et al. |
| 4,985,014 A * | 1/1991 | Orejola .................... 600/16 |
| 4,994,017 A | 2/1991 | Yozu |
| 4,994,078 A | 2/1991 | Jarvik |
| 4,995,857 A | 2/1991 | Arnold |
| 5,009,636 A | 4/1991 | Wortley et al. |
| 5,011,380 A | 4/1991 | Kovacs |
| 5,013,296 A * | 5/1991 | Buckberg et al. .............. 604/44 |
| 5,019,102 A | 5/1991 | Hoene |
| 5,040,944 A | 8/1991 | Cook |
| 5,044,369 A | 9/1991 | Sahota |
| 5,044,897 A | 9/1991 | Dorman |
| 5,049,134 A | 9/1991 | Golding et al. |
| 5,053,004 A | 10/1991 | Markel et al. |
| 5,055,005 A | 10/1991 | Kletschka |
| 5,061,256 A | 10/1991 | Wampler |
| 5,078,741 A | 1/1992 | Bramm et al. |
| 5,079,467 A | 1/1992 | Dorman |
| 5,092,844 A | 3/1992 | Schwartz et al. |
| 5,092,879 A | 3/1992 | Jarvik |
| 5,098,256 A | 3/1992 | Smith |
| 5,112,200 A | 5/1992 | Isaacson et al. |
| 5,112,202 A | 5/1992 | Oshima et al. |
| 5,112,292 A | 5/1992 | Hwang et al. |
| 5,118,264 A | 6/1992 | Smith |
| 5,145,333 A | 9/1992 | Smith |
| 5,147,187 A | 9/1992 | Ito et al. |
| 5,147,388 A * | 9/1992 | Yamazaki .................... 623/3.13 |
| 5,167,223 A | 12/1992 | Koros et al. |
| 5,167,623 A | 12/1992 | Cianci et al. |
| 5,167,628 A * | 12/1992 | Boyles .................... 604/103.07 |
| 5,174,726 A | 12/1992 | Findlay |
| 5,195,877 A | 3/1993 | Kletschka |
| 5,205,721 A | 4/1993 | Isaacson |
| 5,209,650 A | 5/1993 | Lemieux |
| 5,234,456 A | 8/1993 | Silvestrini |
| 5,275,580 A | 1/1994 | Yamazaki |
| 5,282,849 A | 2/1994 | Kolff et al. |
| 5,286,254 A * | 2/1994 | Shapland et al. .............. 604/21 |
| 5,290,227 A | 3/1994 | Pasque |
| 5,295,958 A | 3/1994 | Shturman |
| 5,324,177 A | 6/1994 | Golding et al. |
| 5,326,344 A | 7/1994 | Bramm et al. |
| 5,344,443 A | 9/1994 | Palma et al. |
| 5,360,317 A | 11/1994 | Clausen et al. |
| 5,368,438 A | 11/1994 | Raible |
| 5,370,509 A | 12/1994 | Golding et al. |
| 5,370,610 A | 12/1994 | Reynolds |
| 5,376,114 A | 12/1994 | Jarvik |
| 5,380,276 A | 1/1995 | Miller et al. |
| 5,385,581 A | 1/1995 | Bramm et al. |
| 5,393,207 A | 2/1995 | Maher et al. |
| 5,399,074 A | 3/1995 | Nose et al. |
| 5,399,145 A | 3/1995 | Ito et al. |
| 5,441,535 A | 8/1995 | Takahashi et al. |
| 5,443,503 A | 8/1995 | Yamane |
| 5,456,667 A | 10/1995 | Ham et al. |
| 5,458,574 A * | 10/1995 | Machold et al. ........ 604/101.03 |
| 5,470,208 A | 11/1995 | Kletschka |
| 5,478,309 A * | 12/1995 | Sweezer et al. ............ 604/6.14 |
| 5,480,380 A | 1/1996 | Martin |
| 5,503,615 A | 4/1996 | Goldstein |
| 5,507,629 A | 4/1996 | Jarvik |
| 5,527,159 A | 6/1996 | Bozeman, Jr. et al. |
| 5,531,789 A | 7/1996 | Yamazaki et al. |
| 5,558,634 A | 9/1996 | Mitchell |
| 5,575,630 A | 11/1996 | Nakazawa et al. |
| 5,588,812 A | 12/1996 | Taylor et al. |
| 5,613,935 A | 3/1997 | Jarvik |
| 5,647,358 A | 7/1997 | Vilasi |
| 5,674,198 A * | 10/1997 | Leone .................... 604/101.05 |
| 5,688,245 A * | 11/1997 | Runge .................... 604/151 |
| 5,695,471 A | 12/1997 | Wampler |
| 5,707,218 A | 1/1998 | Maher et al. |
| 5,727,569 A | 3/1998 | Benetti et al. |
| 5,738,649 A * | 4/1998 | Macoviak .................... 604/43 |
| 5,741,234 A | 4/1998 | Aboul-Hosn |
| 5,765,568 A | 6/1998 | Sweezer, Jr. et al. |
| 5,766,209 A | 6/1998 | Devonec |
| 5,782,797 A | 7/1998 | Schwich, Jr. et al. |
| 5,792,106 A * | 8/1998 | Mische .................... 604/103.01 |
| 5,800,375 A | 9/1998 | Sweezer et al. |
| 5,810,757 A | 9/1998 | Sweezer, Jr. et al. |
| 5,820,586 A * | 10/1998 | Booth et al. ................. 604/509 |
| 5,911,685 A * | 6/1999 | Siess et al. .................... 600/16 |
| 5,976,103 A | 11/1999 | Martin |
| 6,083,260 A | 7/2000 | Aboul-Hosn |
| 6,086,570 A | 7/2000 | Aboul-Hosn et al. |
| 6,113,536 A | 9/2000 | Aboul-Hosn et al. |
| 6,123,725 A | 9/2000 | Aboul-Hosn |
| 6,152,704 A | 11/2000 | Aboul-Hosn et al. |
| 6,176,844 B1 * | 1/2001 | Lee .................... 604/101.04 |
| 6,210,133 B1 | 4/2001 | Aboul-Hosn et al. |
| 6,210,397 B1 | 4/2001 | Aboul-Hosn et al. |
| 6,228,063 B1 | 5/2001 | Aboul-Hosn |
| 6,234,960 B1 | 5/2001 | Aboul-Hosn et al. |
| 6,287,319 B1 | 9/2001 | Aboul-Hosn et al. |

| | | | |
|---|---|---|---|
| 6,295,877 | B1 | 10/2001 | Aboul-Hosn et al. |
| 6,395,026 | B1 | 5/2002 | Aboul-Hosn et al. |
| 6,532,964 | B2 | 3/2003 | Aboul-Hosn et al. |
| 2003/0023201 | A1 | 1/2003 | Aboul-Hosn et al. |
| 2003/0205233 | A1 | 11/2003 | Aboul-Hosn et al. |

FOREIGN PATENT DOCUMENTS

| | | |
|---|---|---|
| CA | 1 308 319 | 10/1992 |
| CA | 1 323 467 | 10/1993 |
| CA | 1 328 708 | 4/1994 |
| DE | 2233 293 | 1/1973 |
| DE | 24 53 296 | 5/1976 |
| EP | 280 225 | 8/1988 |
| EP | 0157871 B1 | 7/1990 |
| EP | 0445782 | 9/1991 |
| EP | 0157859 | 4/1992 |
| EP | 0396575 | 3/1994 |
| EP | 0397668 | 3/1994 |
| EP | 0611580 | 8/1994 |
| EP | 0478635 | 12/1994 |
| EP | 0629412 | 12/1994 |
| EP | 0397720 | 3/1995 |
| EP | 0659443 | 6/1995 |
| EP | 0591208 | 11/1995 |
| EP | 0699447 | 3/1996 |
| EP | 0611580 | 12/1996 |
| EP | 0 768 091 | 4/1997 |
| JP | 5071492 | 3/1993 |
| RU | 286 145 | 1/1971 |
| RU | 545 358 | 7/1977 |
| WO | WO 85/01432 | 4/1985 |
| WO | WO 88/07842 | 10/1988 |
| WO | WO 89/04644 | 6/1989 |
| WO | WO 89/04645 | 6/1989 |
| WO | WO 89/05668 | 6/1989 |
| WO | WO 89/07427 | 8/1989 |
| WO | WO 90/15640 | 12/1990 |
| WO | WO 91/01584 | 2/1991 |
| WO | WO 92/02263 | 2/1992 |
| WO | WO 92/03181 | 3/1992 |
| WO | WO 92/06297 | 4/1992 |
| WO | WO 93/07388 | 4/1993 |
| WO | WO 93/20860 | 10/1993 |
| WO | WO 94/06486 | 3/1994 |
| WO | WO 94/09274 | 4/1994 |
| WO | WO 94/09835 | 5/1994 |
| WO | WO 94/13955 | 6/1994 |
| WO | WO 95/00185 | 1/1995 |
| WO | WO 85/01436 | 4/1995 |
| WO | WO 95/28185 | 10/1995 |
| WO | WO96/18358 | 8/1996 |
| WO | WO97/40751 | 11/1997 |
| WO | WO99/02204 | 1/1999 |
| WO | WO99/65546 | 12/1999 |
| WO | WO00/12148 | 3/2000 |
| WO | WO00/18448 | 4/2000 |
| WO | WO00/19097 | 4/2000 |
| WO | WO00/69489 | 11/2000 |

OTHER PUBLICATIONS

Takano, Hisateru, et al., "Ventricular Assist Systems: Experience in Japan with Toyobo Pump and Zeon Pump", Annals of Thoracic Surgery, 1996; 61:317–22.

Tsukiya, Tomonori, "Use of Motor Current in Flow Rate Measurement for the Magnetically Suspended Centrifugal Blood Pump", Artificial Organs, vol. 21, No. 5, pp. 396–401, 1997.

Allaire, P.E., et al., "Prototype Continuous Flow Ventricular Assist Device Supported on Magnetic Bearings", Artificial Organs, vol., No. 6, pp. 582–590, 1996.

Anai, Hirofumi, et al., "Relationship Between Pump Speed Design and Hemolysis in an Axial Flow Blood Pump", Artificial Organs, vol. 20, No. 6, pp. 564–567, 1996.

Andrade, Aron, et al., "Characteristics of a Blood Pump Combining the Centrifugal and Axial Pumping Principles: The Spiral Pump", Artificial Organs, vol. 20, No. 6, pp. 605–612, 1996.

Burgreen, Greg W., et al., "A Design Improvement Strategy for Axial Blood Pumps Using Computational Fluid Dynamics", ASAIO Journal; 42:M354–M360, 1996.

Kaufmann, Ralf, et al., "The Implantable Fuzzy Controlled Helmholtz–Left Ventricular Assist Device: First in Vitro Testing", Artificial Organs, vol. 21, No. 2, pp. 131–137, 1997.

Kawahito, K., et al., "Ex Vivo Evaluation of the NASA/DeBakey Axial Flow Ventricular Assist Device", ASAIO Journal; 42:M754–M757, 1996.

Khanwilker, Pratap, et al., "Using Hybrid Magnetic Bearings to Completely Suspend the Impeller of a Ventricular Assist Device", Artificial Organs, vol. 20, No. 6, pp. 597–604, 1996.

McCarthy, Patrick M., et al., "Permanent Mechanical Circulatory Support With an Implantable Left Ventricular Assist Device", Annals of Thoracic Surgery; 63:1458–61, 1997.

Nishimura, Kazunobu, et al., "Development of a Magnetically Suspended Centrifugal Pump as a Cardiac Assist Device for Long–Term Application", ASAIO Journal pp. 68–71, 1996.

Kubo, Hironao, "Marine Propellers: The Latest Topics", Artificial Organs, vol. 21, No. 2, pp. 109–113, 1996.

Nakazawa, Tadashi, et al., "The Development of Pivot Bearing Supported Sealless Centrifugal Pump for Ventriucular Assist", Artificail Organs, vol. 20, No. 6, pp. 485–490, 1996.

Nakazawa, Tadashi, et al., "The Effect of the Impeller–Drive Magnetic Coupling Distance on Homolysis in a Compact Centrifugal Pump", Artificial Organs, vol. 20, No. 3, pp. 252–257, 1996.

Rosenfeldt, Franklin L., et al., "A Novel Valveless Rotary Pump for Cardiac Assist", Artificial Organs, vol. 21, No. 5, pp. 420–425, 1997.

Daily, Bill B., et al. "Pierce–Donarchy Pediatric VAD: Process in Development", Annals of Thoracic Surgery; 61:437–443, 1996.

Golding, Leonard A.R., et al., "The Cleveland Clinic Rotodynamic Pump Program", Artificial Organs, vol. 20, No. 6, pp. 481–484, 1996.

Hart, Robert M., et al., "A Magnetically Suspended and Hydrostatically Stabilized Centrifugal Blood Pump", Artificial Organs, vol. 20, No. 6, pp. 591–596, 1996.

* cited by examiner

SINGLE PORT CARDIAC SUPPORT APPARATUS

This application is a divisional of application under 37 CFR 1.53(b) of U.S. patent application Ser. No. 08/891,456 filed on Jul. 11, 1997 now U.S. Pat. No. 6,123,725.

BACKGROUND OF THE INVENTION

1. Field of the Invention

The present invention relates generally to apparatus and method for providing cardiac support during cardiac surgery. More particularly, the present invention relates to such apparatus and method for providing cardiac support which are less traumatic and invasive.

2. Description of the Related Art

When it is necessary to perform cardiac surgery, surgery has heretofore been accomplished by major open-heart surgical procedure, requiring general anesthesia and full cardio-pulmonary bypass (CPB). Such surgery usually includes about three weeks of hospitalization and months of recuperation. Average mortality rate for this procedure is approximately 1% with complication rate being substantially higher. Descriptions of open heart procedure can be found in *Gibbon's* Surgery of the Chest $5^{th}$ Edition, (David C. Sabiston, Jr., M.D., Frank D. Spencer, M.D. 1990, Vol. 11, Ch. 52, pp. 1, 56–61, 596, and Textbook of Interventional Cardiology, Eric. J. Topol, 1990, Chs. 43–44, pp. 831–867).

Coronary artery bypass graft (CABG) procedure is one type of open chest surgical technique used to treat coronary artery disease. During the CABG procedure, the patient's sternum must be opened with the chest spread apart to provide access to the heart. The patient's blood is cooled and diverted from the patient's lung to an artificial oxygenator. A source of arterial blood is then connected to a coronary artery downstream from the occlusion while the patient undergoes cardiac arrest and is supported by a CPB circuit. The source of blood is often the left or right internal mammary artery and the target coronary artery is the anterior or posterior arteries which might be narrowed or occluded.

While very effective in many cases, the use of open chest surgery is very traumatic to the patient. The procedure requires immediate post-operative care in an intensive care unit. The total period for hospitalization may be seven to ten days, while the total recovery period may be as long as six to eight weeks. In addition, open-heart procedure requires the use of CPB which continues to represent a major assault on a host of body systems. For example, in up to 24% of the open chest coronary artery bypass surgeries performed in the United States, there is a noticeable degradation of the patient's mental faculties following such surgeries. This degradation is commonly attributed to cerebral arterial blockage from debris and emboli generated during the surgical procedure.

In addition, much post-operative morbidity, and ome mortality, is attributed to the shortcomings of PB.

SUMMARY OF THE INVENTION

It is an object of the present invention to provide an apparatus which provides cardiac support during cardiac surgery.

It is another object of the present invention to provide such an apparatus which is less traumatic and invasive to the patient than current apparatuses used today.

It is a further object of the present invention to provide a method for providing cardiac support using the features described herein.

These and other objects are met by providing an apparatus that is used extravascularly, possibly transvalvularly, and requires only one incision into a major blood vessel or heart chamber. The apparatus includes an elongated inner cannula which is inserted through a portal formed in a major blood vessel or heart chamber. Disposed coaxially over the inner cannula is an outer conduit or cannula. A blood pump, such as the reverse flow blood pump disclosed herein, is communicatively coupled between the proximal openings on the inner cannula and outer conduit. The blood pump may be of one cannula to the distal end of the other cannula. The distal openings on the inner cannula and outer conduit are spaced apart and disposed either in different blood vessels or transvalvularly in the heart.

In this fashion, the apparatus of the present invention may be used in both right-heart and left-heart support applications. For right-heart cardiac support, by way of example only, the outer cannula may be secured within a portal formed in the wall of the pulmonary artery such that its distal opening is positioned within the pulmonary artery, while the inner cannula is extended through the outer conduit and pulmonic valve such that its distal opening is positioned within the right ventricle. The blood pump may then be operated to re-route blood from the right ventricle into the pulmonary artery to assist or replace right-heart function. For left-heart cardiac support, by way of example only, the outer conduit may be secured within a portal formed in the wall of the aorta such that its distal opening is positioned within the aorta, while the inner cannula is extended through the outer cannula, the aortic valve, the left ventricle, and the mitral valve such that its distal opening is positioned in the left atrium. The blood pump may then be operated to re-route blood from the left atrium into the aorta to assist or replace left-heart function.

Optional balloons may be selectively inflated on the outside surface of the inner cannula or outer conduit which act to seal off the passageway between the sides of the blood vessel and the cannula, to cool adjacent tissue, or to deliver drugs to adjacent tissue.

A method of providing cardiac support is also provided which involves the features set forth above regarding the apparatus of the present invention.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENT(S)

Figure 1:
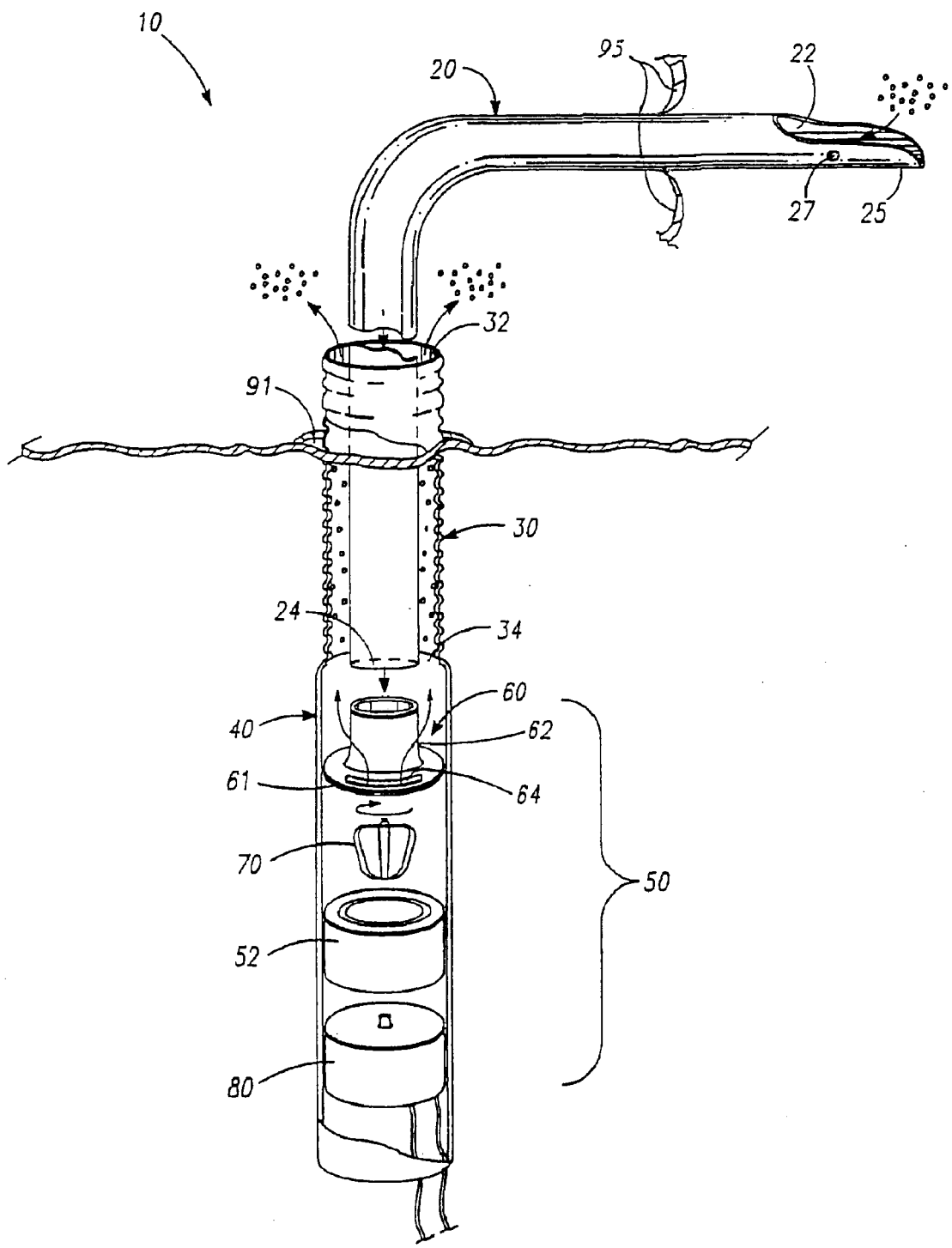
FIG. 1 is a perspective view, partially in section, of the cardiac support apparatus disclosed herein being installed through a portal formed in the major blood vessel with the distal opening of the outer conduit disposed just inside the portal and the inner cannula being disposed transvalvularly in a heart chamber.

Referring to accompanying FIGS. 1–7, therein is shown a cardiac support apparatus, generally referred to as 10, designed to provide cardiac support (right-heart and/or left-heart) during cardiac surgery. The cardiac support apparatus 10 of the present invention generally includes an inner conduit or cannula 20, an outer conduit or cannula 30, and a blood pump 50. The inner cannula 20 has a distal opening 22 that, in use, is positioned to extend past the distal opening 32 of the outer conduit 30. The blood pump 50 is communicatively coupled between the inner cannula 20 and outer conduit 30 to selectively transport blood from one distal opening to the other distal opening. By using such an arrangement, only one portal is required into a major blood vessel or heart chamber.

In the embodiments shown herein, the inner cannula 20 is shown and described as an inlet conduit designed to deliver blood to the pump 50 while the outer conduit 30 is designed to transport blood away from the pump 50. It should be understood, however that the relative functions of the inner cannula and outer conduit may be exchanged depending on the desired positions of the distal openings of the inner cannula 20 and outer conduit 30 and the direction of the flow of blood by the pump 50.

Figure 6:
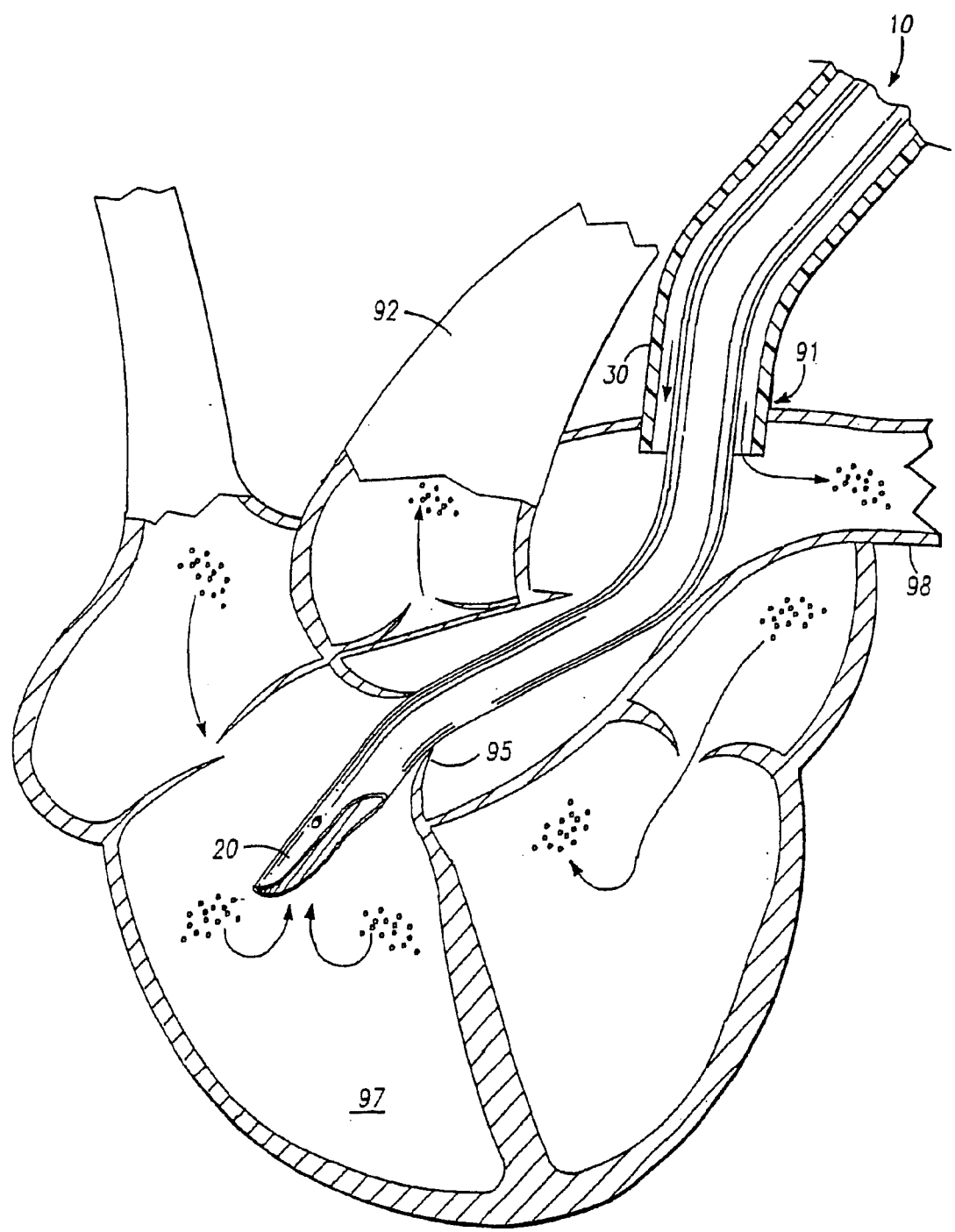
FIG. 6 is an illustration of the heart showing a portal formed in the pulmonary artery with the distal end of the outer conduit extending therethrough and the inner cannula being extending through the pulmonic valve and terminating in the right ventricle.

The inner cannula 20 has a distal opening 22 and a proximal opening 24. During use, the distal opening 22 is disposed in a major blood vessel, such as the aorta or in the right ventricle 97 as shown in FIG. 6. When blood enters the distal opening 22, it is transported through the inner cannula 20 to the pump 50. The pump 50 then forces the blood through the outer conduit 30 to a downstream located blood vessel or chamber.

The inner cannula 20 is tubular and preferably made of flexible, bio-compatible material such as silicone, and reinforced with other material, such as steel wire, to provide sufficient radial stiffness to resist collapsing. The tip 25 of the inner cannula 20 is not reinforced and chambered to provide greater flexibility to improve advancement of the inner cannula 20 through small vessels or chambers and prevent trauma to surrounding tissue. Inner cannula 20 has a plurality of orifices 27 formed near its tip 25 to allow blood to flow into the inner cannula 20 when the distal opening 22 is occluded. During use, a catheter or guide wire can also be extended through the opening 24 which enables the inner cannula 20 to be disposed at a desired location in the body. The inner cannula 20 can have a permanent bend formed therein curved 10 and 20 degrees to facilitate installation and removal from a blood vessel or chamber. The inner cannula 20 may also have radiopaque material added or printed on its surface of visibility when exposed to X-ray radiation.

The outer conduit 30 is tubular and made of flexible, bio-compatible material such as silicone, and reinforced with other material, such as steel wire, to provide sufficient radial stiffness to resist collapsing. The outer conduit 30 has a sufficient inside diameter so that the inner cannula 20 may be coaxially aligned therein and a blood flow passage 65 is created between the outside surface of the inner cannula 20 and the inside surface of the outer conduit 30. In the embodiment shown in FIG. 1, the distal opening 32 of the outer conduit 30 is extended through a portal 91 thereby creating a closed circuit between the inner cannula 20 and outer conduit 30. In the preferred embodiment, the outer conduit 30 is an introducer, a cannula, or a vascular graft, such as DACRON™ graft, or any other vascular graft available commercially and used for anastomosis.

The pump 50 is, by way of example only, a reverse axial flow pump with coaxially aligned inlet and outlet ports formed therein. Pump 50 includes a rotor 70 axially aligned inside a cylindrical-shaped housing body 52. The rotor 70 is connected to a drive shaft 81 which is rotated at high speed by the driving unit 80. The distal opening of the housing body 52 is covered with a housing cap 60. The housing cap 60 is preferably made of stainless steel or a rigid polymer with a plurality of outflow windows 64 formed therein. The outflow windows 64 are radially aligned around the inlet neck 62. The housing body 52 is cylindrical-shaped and includes a longitudinally aligned inlet tube 55. The inlet tube 55 is integrally attached at one end to the base plate 53 and includes a centrally aligned distal opening 56 and a plurality of radially aligned cut-outs 57. Disposed longitudinally inside the inlet tube 55 is the rotor 70.

During operation, the rotor 70 is rotated which forces blood delivered to the inlet tube 55 through the cut-outs 57. The outside diameter of the inlet tube 55 is smaller than the inside diameter of the housing body 52 thereby creating a passageway 59 between the inlet tube 55 and the housing body 52. Attached over the distal opening of the housing body 52 is a housing cap 60. The housing cap 60 includes a circular base member 61 designed to attach tightly over the housing body 52. A cylindrical inlet neck 62 is perpendicular and centrally aligned on the base member 61. A plurality of outflow windows 64 are radially aligned on the base member 61 outside the inlet neck 62. The outer diameter of the inlet neck 62 is smaller than the inside diameter of the outer conduit 30 thereby creating a second passageway 65 for blood to flow through. The passageway 59 and the outflow windows 64 of the housing cap 60 are aligned when the housing cap 60 and the housing body 52 are assembled.

Figure 2:
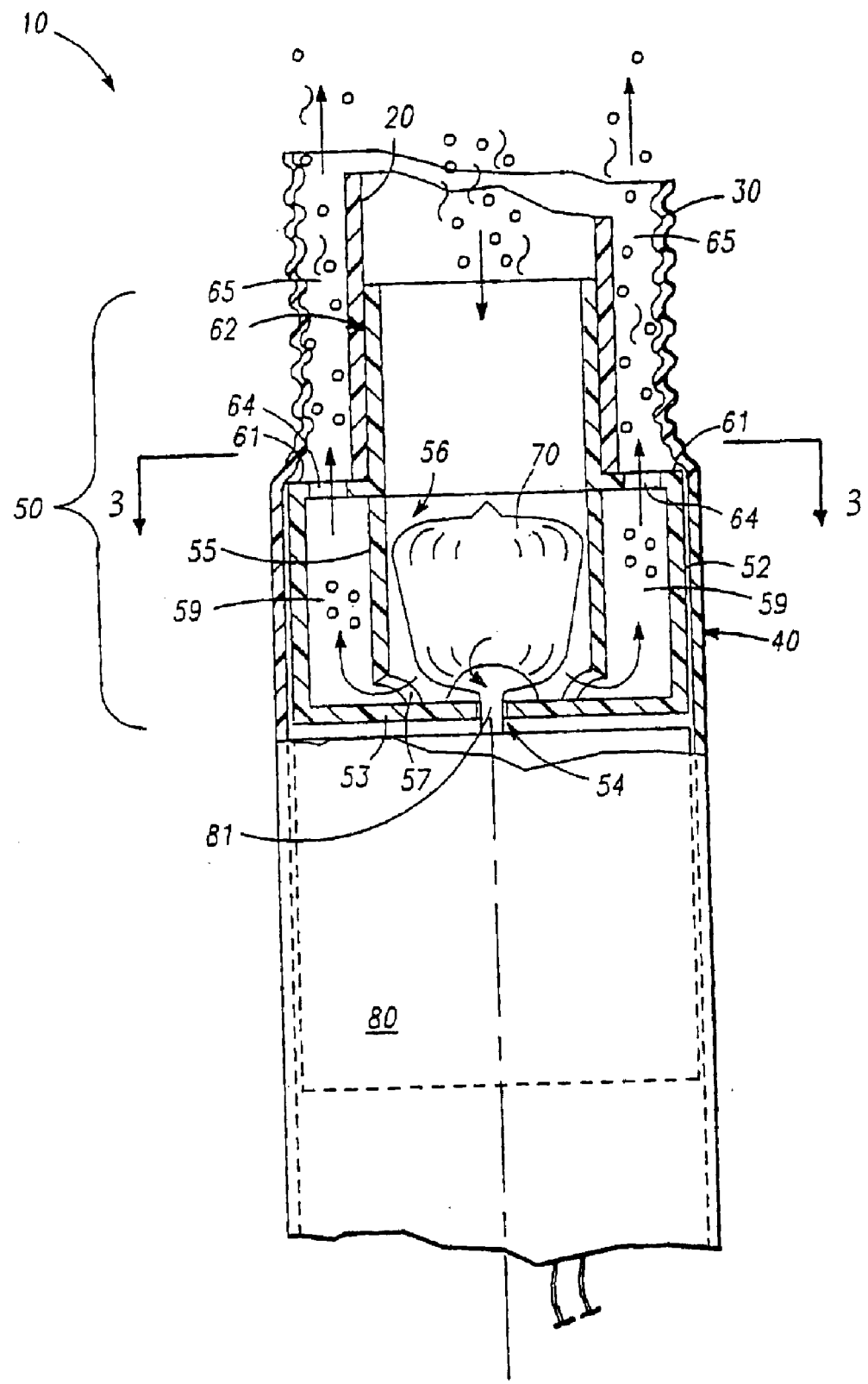
FIG. 2 is a side elevational view, partially in section, of the cardiac support apparatus.
Figure 3:
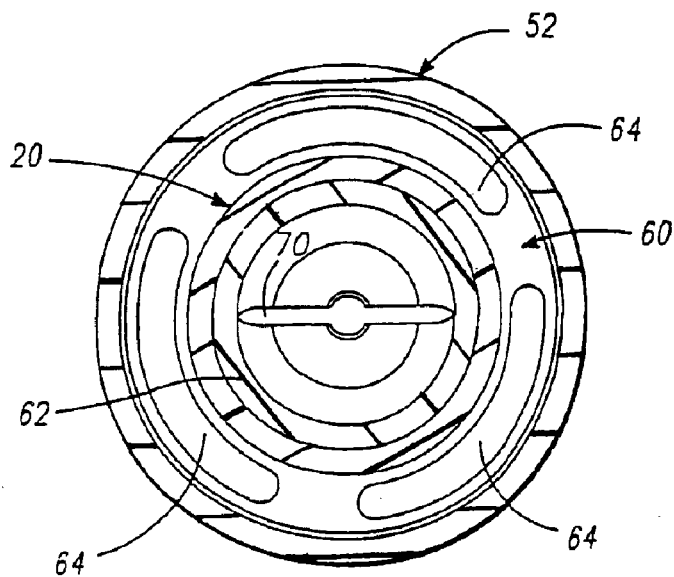
FIG. 3 is a sectional view of the apparatus taken along lines 3—3 in FIG. 2.
Figure 4:
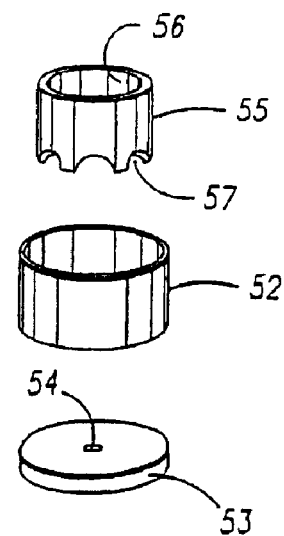
FIG. 4 is an exploded, perspective view of the pump's housing body with an inlet tube and base plate.
Figure 5:
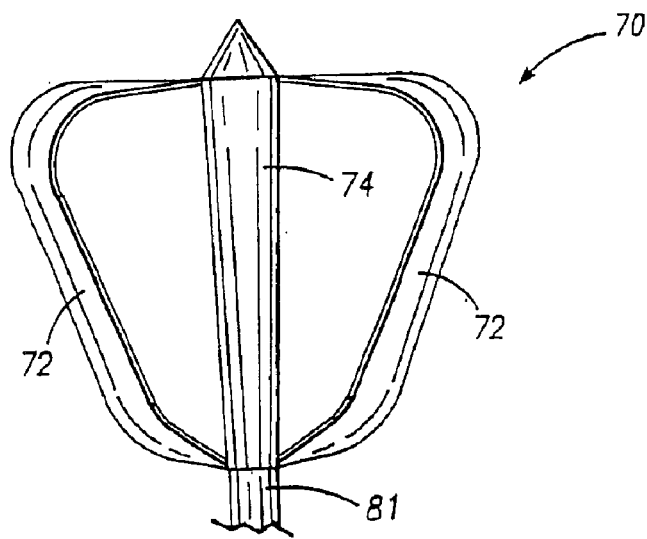
FIG. 5 is a side elevational view of the rotor.

As shown in FIGS. 1 and 2, the apparatus 10 is assembled in an optional elongated, cylindrical body 40 which connects to the proximal opening 34 of the outer conduit 30 designed to house the pump 50 and the drive unit 809. During use, the cylindrical body 40 acts as a handle to enable the apparatus 10 to be placed in a desired location. In other embodiments, not shown, the pump 50 may be sealed and attached to the outer conduit 30 with the drive unit 80 located externally.

During installation, the distal openings 22, 32, of the inner cannula 20 and outer conduit 30, respectively, are adjusted to be spaced apart and located in different blood vessels or opposite sides of a heart valve thereby enabling blood to be pumped from one blood vessel or chamber to another. The inner cannula 20 and outer conduit 30 are coaxially aligned and have sufficient length so that only one portal opening is required into the major blood vessel or chamber.

The placement of the apparatus 10 requires the anastomosis of the distal end of the outer conduit to the sides of the targeted blood vessel or chamber using thoracoscopic suturing, or microstapling. Prior to suturing the outer conduit 30 to the blood vessel, the blood vessel can be isolated using a "C" clamp or the use of thoracoscopic clamps best described in Evard. P. et al. in U.S. Pat. No. 5,425,705 or similar clamps capable of passing small ports on the patient's body and could isolate a section of a vessel without complete occlusion of the vessel in question.

FIG. 6 is an illustration of the cardiac support apparatus 10 being used to provide cardiac support to the right side of the heart by pumping blood from the right ventricle 97 to the pulmonary artery 98. In this instance, a portal 91 is formed in the pulmonary artery 98 through which the distal end of the outer conduit 30 is extended. The inner cannula 20 is then inserted into the portal 91, through the pulmonic valve 95 and into the right ventricle 97. It will be appreciated that this same right-heart cardiac support could be accomplished (and is contemplated as being part of the present invention) by securing the outer conduit 30 within a portal formed in the wall of the right atrium, right ventricle, or atrial appendage such that its distal end is positioned in the right atrium or right ventricle, while the inner cannula 20 is extended therethrough such that its distal end is positioned within the pulmonary artery. In this arrangement, the pump 50 would reroute blood from the outer conduit 30 into the inner cannula 20 for delivery into the pulmonary artery for right-heart cardiac support.

Figure 7:
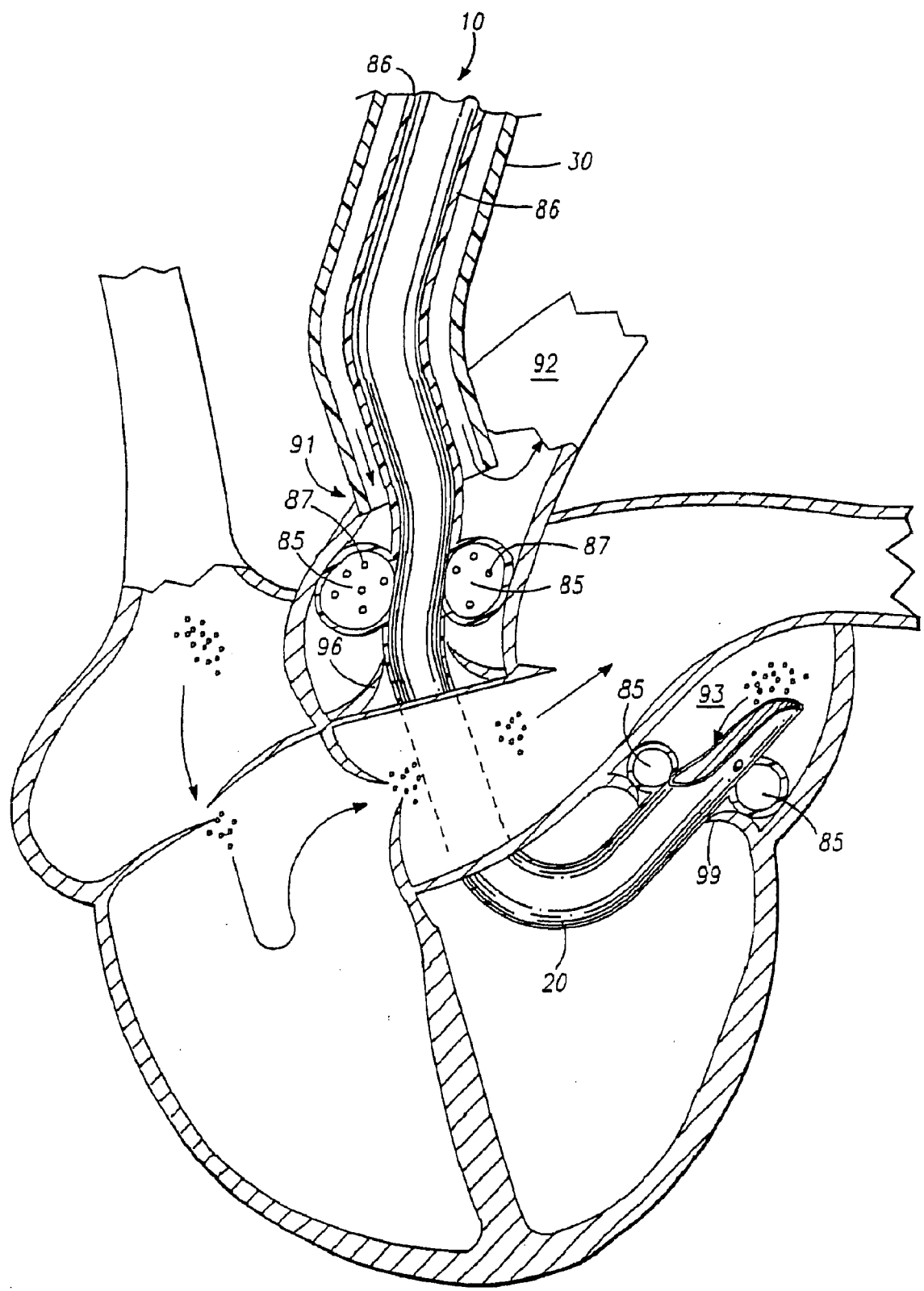
FIG. 7 is an illustration of the heart showing a portal formed in the aorta with the distal end of the outer conduit extending therethrough and the inner cannula being extended through the aortic valve, left ventricle, and mitral valve and terminating in the left atrium.

FIG. 7 is an illustration showing the apparatus 10 with the outer conduit 30 being attached to a portal 91 formed in the aorta 92 and the inner cannula 20 being extended through the portal 91, then the aortic and mitral valves 96, 99, respectively, and into the left atrium. It will be appreciated that this same left-heart cardiac support could be accomplished (and is contemplated as being part of the present invention) by securing the outer conduit 30 within a portal formed in the wall of the left atrium or left ventricle such that its distal end is positioned in the left atrium or left ventricle, while the inner cannula 20 is extended therethrough such that its distal end is positioned within the aorta. In this arrangement, the pump 50 would reroute blood from the outer conduit 30 into the inner cannula 20 for delivery into the aorta for left-heart cardiac support.

After the portal is created in the desired blood vessel, the outer conduit 30 is then inserted into the portal 91. A suture may be used to hold the outer conduit 30 inside the portal 91. A commercially available high stiffness guide wire may be passed through the outer conduit 30 to which the inlet cannula 20 and pump 50 are attached. The length of the outer conduit 30 must be sufficiently long to accommodate the pump 50. After placing the pump 50 in the outer conduit 30, the outer conduit 30 is filled with a saline solution, the pump 50 is primed if necessary, and air is completely removed from the pump 50 and the outer conduit 30. The driving unit 80 is then installed over the proximal end of the pump 50. A silicone plug or similar hemostasis valve must be used to seal the outer conduit 30 if the driving unit 80 is located externally.

After the installation is completed, the "C" clamp is released gradually and hemostasis at all possible bleeding sites are examined visually or with the aid of a viewing scope inserted into the body. Assuming acceptable hemostasis is achieved, then the "C" clamp 300 may be completely released but kept in a position to clamp the anastomosis site in case of emergency.

At this point, the guide wire can be advanced with the help of imaging techniques to dispose the distal end of the inlet cannula 20 in the desired blood vessel or heart chamber. While positioning the distal end of the inlet cannula 20, the pump 50 may need to be advanced in the outer conduit 30 by pushing the positioning rod into the outer conduit 30. A suture or laproscopic clamping device may then be used to hold the apparatus in place. After securing the apparatus 10, the guide wire is removed from and the pump 50 is activated to initiate blood pumping.

After the pump 50 is activated, a drug known to slow or completely stop the heart can be administered as required. The pumping rate of the pump 50 is then adjusted to maintain sufficient circulation. The pumping rate can also be adjusted to accommodate changes in the circulatory demand. The pump 50 can also be equipped with means (not shown) for measuring blood pressure, the presence of blood at the tip of the inner cannula, or other parameters that could indicate to the treating physician if a change in speed is required. Also, the apparatus 10 may include sensors (not shown) that sense the pressure at the proximal distal opening of the inner cannula 20, wherein a preset pressure change could signal the need to change the pumping capacity of apparatus 10. For example, when the pressure at the distal end of inner cannula 20 decreases by a certain degree, which indicates the commencement of pump suction, a controller used with the apparatus 10 could signal the user or automatically decrease the pump speed to return to a pre-selected pressure at the inner cannula 20.

To remove the apparatus 10, the suture or laproscopic clamping device is first disconnected enabling the apparatus 10 to move. The pump 50 and inner cannula 20 is retracted though the outer conduit 30, the "C" clamp 300 is clamped, thoracoscopically the anastomosis is restored using common thoracoscopic techniques for suturing or stapling, then anastomosis is removed and the patient's skin would is closed using known techniques for wound closure.

Also, as shown in FIG. 7, an optional balloon 85 may be disposed on the outside surface of the inner cannula 20 to seal, or to deliver a cool fluid or medication to the adjacent tissue. The balloon 85 is disposed around the inner cannula 20 and connected to a conduit 86 through which air, a suitable coolant, or medication may be transported to the balloon 85. When the balloon 85 is used to deliver medication, a plurality of perforations 87 may be formed on the surface of the balloon 85 to allow medication to be delivered to the surrounding tissue.

Using the above described apparatus, a method of providing cardiac support is also provided which includes the following steps:

a. selecting a blood flow apparatus including a generally coaxially aligned and slideably arranged inner conduit and outlet conduit, and a blood pump disposed therebetween, the blood pump capable of pumping blood through a body;

b. forming a portal in a blood vessel or heart chamber;

c. securing the outer conduit within the portal;

d. inserting the inner conduit through the portal so that the distal opening of the inner cannula is disposed on an opposite side of a desired heart valve as the distal opening of the outer conduit; and e. activating the pump so that blood is pumped into the distal opening of one of the inner conduit and outer conduit and transported out of the distal opening of the other of the inner conduit and outer conduit.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A method of providing cardiac support comprising the steps of:
   a. selecting a blood flow apparatus including a generally coaxially aligned and slideably arranged inner conduit and outlet conduit, and a blood pump disposed therebetween, the blood pump capable of pumping blood through a body;
   b. forming a portal in a blood vessel;
   c. securing the outer conduit within the portal;
   d. inserting the inner conduit through the outer conduit and advancing the inner conduit through a vessel into the heart and through a desired heart valve so that the distal opening of the inner cannula is disposed on an opposite side of the desired heart valve as the distal opening of the outer conduit; and
   e. activating the pump so that blood is pumped into the distal opening of one of the inner conduit and outer conduit and transported out of the distal opening of the other of the inner conduit and outer conduit.

2. A method of providing cardiac support comprising the steps of:
   a. selecting a blood flow apparatus including a generally coaxially aligned and slideably arranged inner conduit and outlet conduit, and a blood pump disposed therebetween, the blood pump capable of pumping blood through a body;
   b. forming a portal in a heart chamber;
   securing the outer conduit within the portal;
   d. inserting the inner conduit through the outer conduit so that the distal opening of the inner cannula is disposed on an opposite side of a desired heart valve as the distal opening of the outer conduit; and
   e. activating the pump so that blood is pumped into the distal opening of one of the inner conduit and outer conduit and transported out of the distal opening of the other of the inner conduit and outer conduit.

3. A method of providing cardiac support comprising the steps of:
   a. selecting a blood flow apparatus including a slideably arranged inner conduit and outlet conduit, and a blood pump disposed therebetween, the blood pump capable of pumping blood through a body;
   b. forming a portal in a blood vessel;
   c. securing the outer conduit within the portal;
   d. inserting the inner conduit through the outer conduit and advancing the inner conduit through a vessel into the heart and through a desired heart valve so that the distal opening of the inner cannula is disposed on an opposite side of the desired heart valve as the distal opening of the outer conduit; and
   e. activating the pump so that blood is pumped into the distal opening of one of the inner conduit and outer conduit and transported out of the distal opening of the other of the inner conduit and outer conduit.

4. The method of claim 3 and further, wherein the blood pump is a reverse axial flow blood pump.

5. The method of claim 3 and further, wherein the distal openings of the inner and outer conduits are positioned on either side of the pulmonic valve and the pump operated to provide right-heart cardiac support.

6. The method of claim 3 and further, wherein the distal openings of the inner and outer conduits are positioned on either side of the aortic valve and the pump operated to provide left-heart cardiac support.

7. A method of providing cardiac support comprising the steps of:
   a. selecting a blood flow apparatus including a slideably arranged inner conduit and outlet conduit, and a blood pump disposed therebetween, the blood pump capable of pumping blood through a body,
   b. forming a portal in a heart chamber;
   c. securing the outer conduit within the portal;
   d. inserting the inner conduit through the outer conduit so that the distal opening of the inner cannula is disposed on an opposite side of a desired heart valve as the distal opening of the outer conduit; and
   f. activating the pump so that blood is pumped into the distal opening of one of the inner conduit and outer conduit and transported out of the distal opening of the other of the inner conduit and outer conduit.

* * * * *

UNITED STATES PATENT AND TRADEMARK OFFICE
CERTIFICATE OF CORRECTION

| | |
|---|---|
| PATENT NO. | : 6,858,001 B1 |
| APPLICATION NO. | : 09/669104 |
| DATED | : February 22, 2005 |
| INVENTOR(S) | : Aboul-Hosn |

It is certified that error appears in the above-identified patent and that said Letters Patent is hereby corrected as shown below:

In the Abstract, line 4, please delete "slideably" and insert --slidably--;
In the Abstract, line 9, please delete "the sides surrounding" and insert --the sides of the surrounding--;
After the Abstract, please delete "7 Claims, 5 Drawing Sheets" and insert --10 Claims, 5 Drawing Sheets--;
Column 1, line 55, please delete "ome" and insert --some--;
Column 6, line 28, please delete "skin would" and insert --skin wound--;
Column 6, line 44, please delete "slideably" and insert --slidably--;
Column 6, line 45, please delete "outlet" and insert --outer--;
Column 7, line 5 (Claim 6, line 1), please delete "slideably" and insert --slidably--;
Column 7, line 6 (Claim 1, line 7), please delete "outlet" and insert --outer--;
Column 7, after line 20 (after Claim 1) please insert:
--2. The method of claim 1 and further, wherein the blood pump is a reverse axial flow blood pump.
3. The method of claim 1 and further, wherein the distal openings of the inner and outer conduits are positioned on either side of the pulmonic valve and the pump operated to provide right-heart cardiac support.
4. The method of claim 1 and further, wherein the distal openings of the inner and outer conduits are positioned on either side of the aortic valve and the pump operated to provide left-heart cardiac support.--;
Column 7, line 22 (Claim 2, line 1), please delete "2." and insert --5.--;
Column 7, line 25, please delete "slideably" and insert --slidably--;
Column 7, line 31, before "securing" insert --c.--;
Column 7, line 40 (Claim 3, line 1), please delete "3." and insert --6.--;
Column 8, line 15 (Claim 4, line 1), please delete "4." and insert --7.--;
Column 8, line 15, please delete "3" and insert --6--;
Column 8, line 17 (Claim 5, line 1), please delete "5." and insert --8.--;
Column 8, line 17, please delete "3" and insert --6--;
Column 8, line 22 (Claim 6, line 1), please delete "6." and insert --9.--;
Column 8, line 22, please delete "3" and insert --6--;

Signed and Sealed this
Fifteenth Day of February, 2011

David J. Kappos
*Director of the United States Patent and Trademark Office*

Column 8, line 26 (Claim 7, line 1), please delete "7." and insert --10.--;
Column 8, line 28, please delete "slideably" and insert --slidably--.